(12) United States Patent
O'Shea

(10) Patent No.: US 7,932,079 B2
(45) Date of Patent: Apr. 26, 2011

(54) APPARATUS FOR PRODUCING AND HANDLING A FLOWING SUBSTANCE

(75) Inventor: Mark O'Shea, Dublin (IE)

(73) Assignee: Lifestyle Foods Limited, Dublin (IE)

( * ) Notice: Subject to any disclaimer, the term of this patent is extended or adjusted under 35 U.S.C. 154(b) by 446 days.

(21) Appl. No.: 12/097,903

(22) PCT Filed: May 9, 2006

(86) PCT No.: PCT/IE2006/000054
§ 371 (c)(1),
(2), (4) Date: Oct. 14, 2008

(87) PCT Pub. No.: WO2006/120660
PCT Pub. Date: Nov. 16, 2006

(65) Prior Publication Data
US 2009/0117533 A1 May 7, 2009

(30) Foreign Application Priority Data

May 10, 2005 (IE) .................................. S2005/0294

(51) Int. Cl.
*C12M 1/36* (2006.01)
(52) U.S. Cl. ................ 435/286.5; 435/3; 435/819; 71/8
(58) Field of Classification Search ........... 435/3, 286.5, 435/819; 426/61; 504/117; 71/8; 536/26.42
See application file for complete search history.

(56) References Cited

U.S. PATENT DOCUMENTS

| 3,681,083 A | 8/1972 | Everson |
| 4,354,936 A | 10/1982 | Ishida et al. |
| 4,650,766 A * | 3/1987 | Harm et al. ................ 435/286.6 |

(Continued)

FOREIGN PATENT DOCUMENTS

EP     0154614    9/1985

(Continued)

OTHER PUBLICATIONS

International Search Report And Written Opinion, PCT/IE2006/000054, Aug. 29, 2006.

*Primary Examiner* — William H Beisner
*Assistant Examiner* — Michael Hobbs
(74) *Attorney, Agent, or Firm* — Baker Donelson

(57) ABSTRACT

A system (1) for producing a dough starter culture is provided which comprises a plurality of reservoirs (15) pre-loaded with a small amount ("mother level") of a previously obtained starter culture. Into the reservoirs (15) are inoculated the other ingredients required for the preparation of starter culture and the contents are left to ferment for a specified period of time to produce the required starter culture, which is then discharged as required from each reservoir (15). A "mother level" portion is retained in the reservoirs and is used to produce a next batch of starter culture. The system (1) operates automatically and is programmable so that a first pre-set interval of time which is less then the fermentation time is allowed to elapse from the start of fermentation in a first reservoir (15) before the ingredients are delivered into a succeeding reservoir (15), and a second pre-set interval of time is allowed to elapse after the starter culture is discharged from the first reservoir (15) before a next batch of the ingredients is delivered into the first reservoir (15).

11 Claims, 9 Drawing Sheets

U.S. PATENT DOCUMENTS

| | | |
|---|---|---|
| 4,851,347 A | 7/1989 | Willrett et al. |
| 5,316,905 A | 5/1994 | Mori et al. |
| 5,424,209 A | 6/1995 | Kearney et al. |
| 5,482,723 A | 1/1996 | Sasaki et al. |
| 5,979,300 A | 11/1999 | Donovan et al. |
| 2002/0110905 A1* | 8/2002 | Barbera-Guillem et al. .......... 435/294.1 |
| 2002/0164653 A1* | 11/2002 | Downs ............ 435/7.1 |
| 2003/0228680 A1 | 12/2003 | Kringelum et al. |

FOREIGN PATENT DOCUMENTS

| | | |
|---|---|---|
| EP | 0753573 | 1/1997 |
| GB | 270770 | 5/1927 |
| GB | 2062255 | 5/1981 |
| NL | 8800175 | 8/1989 |
| WO | 2004072271 | 8/2004 |

* cited by examiner

| TIME ZERO - TANK 1 | | | |
|---|---|---|---|
|  | Temperature, °C | Duration, hours | Action |
| 100  Tank pre-loaded with "mother level" of starter | 16 | 1 | Fill tank with flour/water mix at 21°C |
| 101  Tank full | 21 | 10 | Fermentation begins |
| 102  Starter culture ready for use | 16 | 1 | Cool the starter culture to 16°C |
|  | 16 | 3 | Use starter culture within three hours |
| 103  Tank again at "mother level" |  | 3 | Wait three hours before introducing next batch of flour/water mix |
| 104  Repeat cycle |  |  |  |
| 3 HOURS LATER - TANK 2 | | | |
|  | Temperature, °C | Duration, hours | Action |
| 200  Tank pre-loaded with "mother level" of starter | 16 | 1 | Fill tank with flour/water mix at 21°C |
| 201  Tank full | 21 | 10 | Fermentation begins |
| 202  Starter culture ready for use | 16 | 1 | Cool the starter culture to 16°C |
|  | 16 | 3 | Use starter culture within three hours |
| 203  Tank again at "mother level" | 16 | 3 | Wait three hours before introducing next batch of flour/water mix |
| 204  Repeat cycle |  |  |  |

FIGURE 7

| DAY 1 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| Tank 1 | * |   | x | x | x | x | x | x | x | x | x | + | - | - | - | - | - | - | * | x | x | x | x | x |
| Tank 2 |   | x |   |   | x | x | x | x | x | x | x | x | x | x | + | x | x | x | x | x | x | * | x | x |
| Tank 3 |   |   |   | * |   |   | * | x | x | x* | x | x | x | x | x | x | x | + | - | - | - | - | - | - |
| Tank 4 |   |   |   |   |   |   |   |   |   |   |   |   |   | x | x | x | x | x | x | x | x | x | x | + |
| Tank 5 |   |   |   |   |   |   |   |   |   |   |   |   | x* | x | x | x* |   |   | x | x | x | x | x | x |
| Tank 6 |   |   |   |   |   |   |   |   |   |   |   |   |   |   |   |   |   |   | x | x | x | x | x | x |
| Tank 7 |   |   |   |   |   |   |   |   |   |   |   |   |   |   |   | * |   |   | * | x | x | * | x | x |
| Tank 8 |   |   |   |   |   |   |   |   |   |   |   |   |   |   |   |   |   |   |   |   |   |   | x | x |

| DAY 2 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| Tank 1 | x | x | x | x | x | + | - | - | - | - | - | - | * | x | x | x* | x | x | x | x | x | x | x | + |
| Tank 2 | x | x | x | x | x | x | x | x | + | x | x | x | x | x | x | x | x | x | x | x | x | x | x | x |
| Tank 3 | * | x | x | * | x | x | x | x | x | x* | x | x | x | x | x | x | x | x | x | x | x | x* | x | x |
| Tank 4 |   |   |   | - | - | - | - | - | - | - |   | + | - | - | - | - | - | - | - | - | - | - | - | - |
| Tank 5 | + | - | + | x | x | x | x | x | x | x | x | x | x | x | + | x | x | x | x | x | + | x | x | + |
| Tank 6 | x | x | x | x |   | - | - | - | - | x* | x | x | x | x | x | x | x | x | x | x | x | x | x | x |
| Tank 7 | x | x | x | x | x | + | - | - | - | - | - | - | * | x | x | x* | x | x | x | x | x | x | x | x |
| Tank 8 | x | x | x | x | x | x | x | x | + | - | - | - |   |   |   |   |   |   |   |   |   |   |   |   |

| | |
|---|---|
| * | Tank pre-loaded with "mother level" of starter culture |
| | Tank filling time |
| x | Fermentation |
| + | Cooling |
| - | Fermented starter culture used |

FIGURE 8

APPARATUS FOR PRODUCING AND HANDLING A FLOWING SUBSTANCE

This application claims the benefit of PCT/IE2006/000054, filed 9 May 2006 and of Ireland patent application number S2005/0294, filed 10 May 2005.

TECHNICAL FIELD

The present invention relates to a system for producing and handling a flowing substance and in particular to a system for producing and handling a starter culture such as, for example, dough starter culture.

BACKGROUND ART

Starter culture is a very delicate substance comprising microorganisms which process organic matter, to produce compounds useful in dairy, baking, brewing and many other industries. Performance of these microorganisms, and therefore the quality of starter culture is highly dependent on temperature conditions of the environment in which the starter culture is produced. Even slight fluctuations of this temperature may affect the process and the characteristics of the final product may differ from the required ones. Fermentation time is also a very important parameter and must be accurately controlled. In a production line environment, such as for example, a bakery line, it is difficult to provide a large-scale starter culture management system without the need for a large number of staff for such operations as control and monitoring of the process, cleaning, etc. On the other hand, manual operations are prone to mistakes which put the production at risk.

Similar problems exist in production of any flowing substance in a controlled environment on a large scale.

The present invention seeks to alleviate the above disadvantages.

SUMMARY OF THE INVENTION

Accordingly, the invention provides a system for producing and handling a flowing substance comprising:

a mixing vessel for mixing ingredients for use in subsequent preparation of a flowing substance;

a first manifold for transferring the mixed ingredients from the mixing vessel into one of a plurality of reservoirs where the mixed ingredients are combined with an initiating culture;

first regulating means for maintaining predetermined conditions in each reservoir suitable to allow a fermentation process to occur which results in the production after a specified time of a starter culture as a flowing substance having predetermined properties from the initiating culture and the mixed ingredients;

a second manifold for transferring the starter culture from each reservoir to at least one receiving container; and electronic control means for controlling the system so that the system provides delivery of mixed ingredients to each reservoir in a specified sequence so that a first pre-set interval of time elapses from the start of fermentation in a first or subsequent reservoir before the delivery of the mixed ingredients into a succeeding next reservoir, that interval being less than the fermentation time of the starter culture in the preceding reservoir, wherein the electronic control means is adapted to control the system so that the system effects discharge of a desired first portion of the starter culture from a reservoir whilst retaining a second portion therein, said retained second portion comprising an initiating culture for subsequent production in that reservoir of a further batch of starter culture upon introduction of a next load of the mixed ingredients; and to allow a second pre-set delay interval to elapse after the discharge before introducing the next load of the mixed ingredients into the reservoir;

first propelling means for transferring mixed ingredients into each reservoir via the first manifold and second propelling means for transferring the starter culture produced in the reservoir into the receiving container via the second manifold, wherein the electronic control means is programmed to control the second propelling means to discharge the starter culture produced in a reservoir, save for the second portion of the starter culture which remains in the reservoir and is retained for a subsequent cycle of production of starter culture in this reservoir, the remaining second portion being sufficient to serve as initiating culture for the subsequent cycle; and a sensor means connected between the reservoir and the electronic control means for enabling the electronic control means to determine the quantity of starter culture in the reservoir and to prevent the quantity falling below a predetermined quantity on actuation of the second propelling means.

In another aspect, the invention provides a method for producing a starter culture in the above described system having a plurality of reservoirs comprising the steps of:

(a) pre-loading the culture reservoirs with a desired amount of initiating culture maintained at an oppression temperature;

(b) filling at least one first reservoir with a relevant amount of aqueous medium/flour mix;

(c) allowing the contents of the first reservoir to ferment at a specified fermentation temperature for a pre-set fermentation time interval to obtain a fermented starter culture;

(d) cooling the so obtained fermented starter culture in the first reservoir to an oppression temperature to stop the fermentation process;

(e) discharging a first portion of the starter culture from the first reservoir-whilst retaining a desired second portion therein, said retained second portion comprising an initiating culture for subsequent production in the first reservoir of a further batch of starter culture upon introduction of a next load of aqueous medium/flour mix;

(f) upon expiry of a first pre-set delay interval from the start of fermentation in the first reservoir, filling a subsequent reservoir with a relevant amount of aqueous medium/flour mix;

(g) allowing a second pre-set delay interval to elapse after the discharge before introducing the next load of aqueous medium/flour mix into the first reservoir; and (h) repeating steps c) to f) in respect of the subsequent reservoir as if it were the first reservoir.

BRIEF DESCRIPTION OF THE DRAWINGS

In the drawings:

FIG. 7 is a flow chart illustrating stages of a starter culture production cycle of two fermentation tanks of an eight-tank system and a time sequence between the production cycle;

FIG. 8 shows two tables showing a 24 hour schedule of production cycles of eight fermentation tanks in an eight-tank system for two subsequent days.

DETAILED DESCRIPTION

Figure 1:
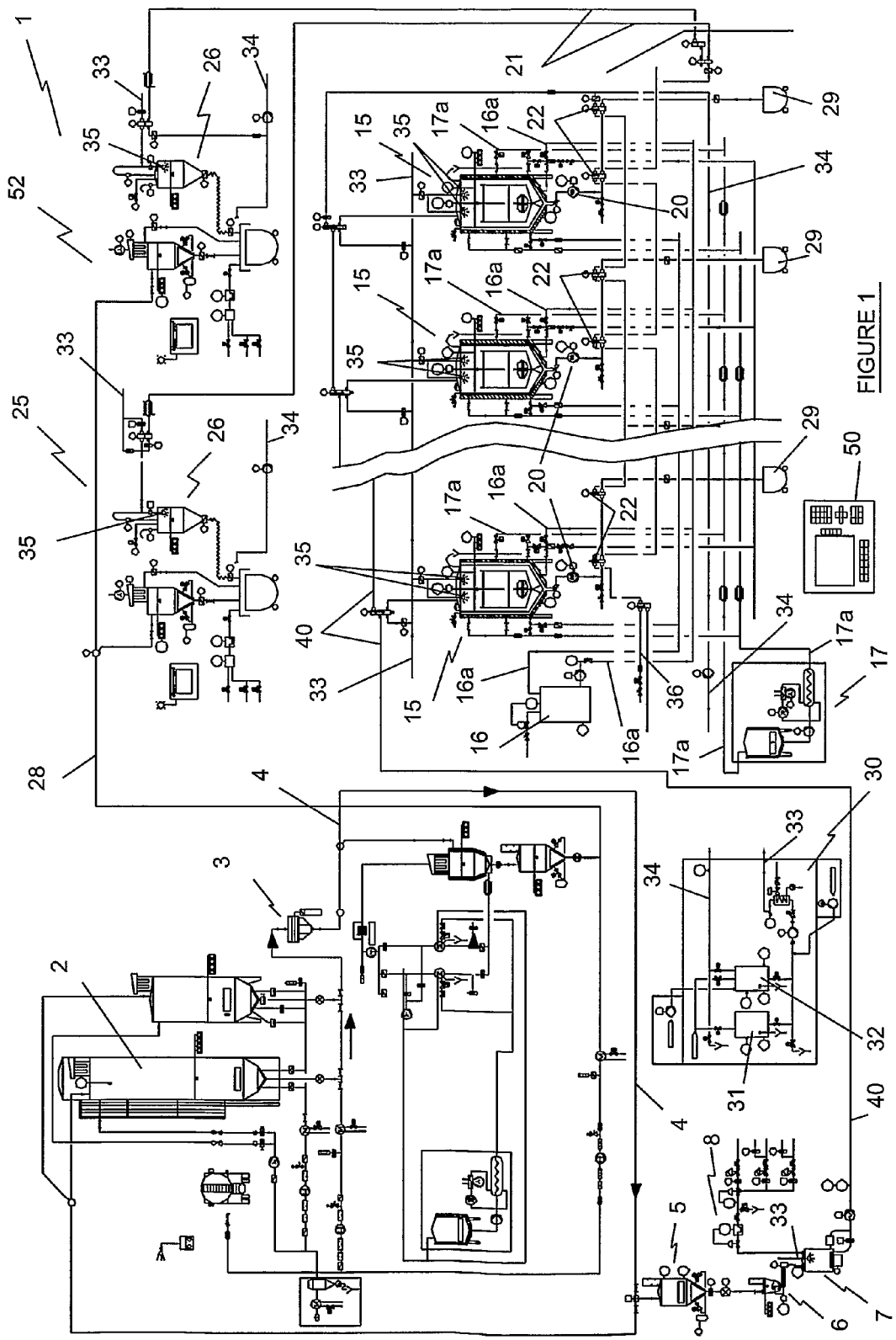
FIG. 1 is a schematic plan view of a system according to the invention.
Figure 2:
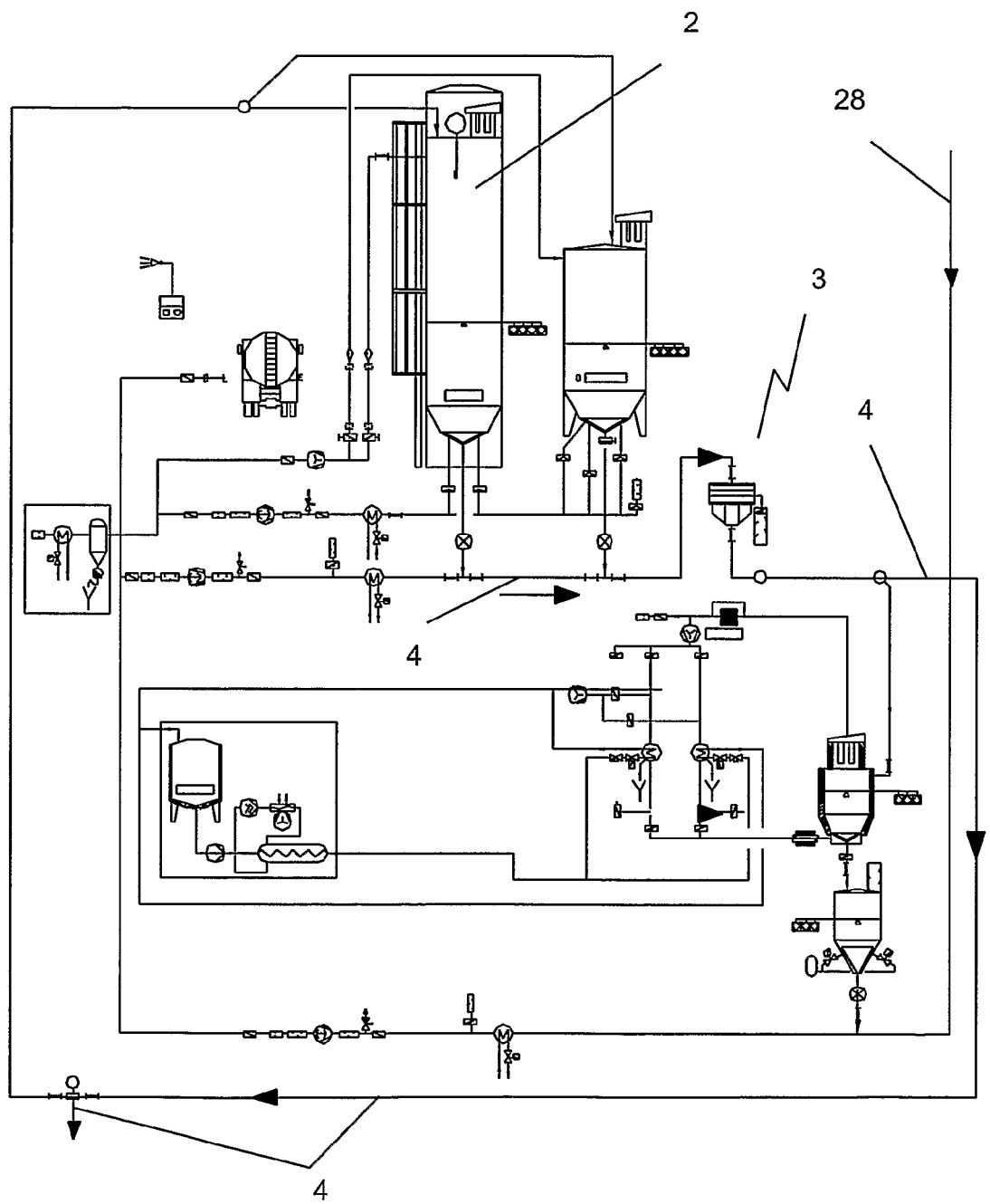
FIG. 2 is an enlarged portion of FIG. 1 showing a flour silo of the system.

The present invention will now hereinafter be described with reference to the accompanying drawings which show, by way of example only, one embodiment of a system for producing and handling starter culture in accordance with the invention.

As discussed in detail below, the invention provides a system for producing and handling a flowing substance comprising mixing vessel for mixing ingredients for use in subsequent preparation of a flowing substance;

a first manifold for transferring the mixed ingredients from the mixing vessel into one of a plurality of reservoirs where the mixed ingredients are combined with an initiating culture;

a first regulating means for maintaining predetermined conditions in each reservoir suitable to allow a fermentation process to occur which results in the production after a specified time of a starter culture as a flowing substance having predetermined properties from the initiating culture and the mixed ingredients;

a second manifold for transferring the starter culture from each reservoir to at least one receiving container; and an electronic control means operable to control the system to provide delivery of mixed ingredients to each reservoir in a specified sequence so that a first pre-set interval of time elapses from the start of fermentation in a first or subsequent reservoir before the delivery of the mixed ingredients into a succeeding next reservoir, that interval being less than the fermentation time of the starter culture in the preceding reservoir.

Ideally, the electronic control means is operable to control the system so as to effect discharge of a desired first portion of the starter culture from a reservoir whilst retaining a desired second portion therein, said retained second portion comprising an initiating culture for subsequent production in that reservoir of a further batch of starter culture upon introduction of a next load of the mixed ingredients; and to allow a second pre-set delay interval to elapse after the discharge before introducing the next load of the mixed ingredients into the reservoir.

Such arrangement of the system ensures availability of adequate supplies of starter culture of required quality during a specified period of time, for example during a production run of a bakery line, such as a five-day production week. Any number of reservoirs greater than one may be employed in such a system. For example, eight reservoirs have been found to suit a five-day production plan and a fermentation time of twelve hours in each reservoir.

Conveniently, the system comprises a first measuring means at each of the reservoirs for measuring required quantities of the ingredients delivered into each reservoir; a second measuring means for measuring required quantities of the ingredients in the mixing vessel; and a third measuring means for measuring a quantity of the starter culture delivered into the at least one receiving container.

Ideally, the system further comprises a second regulating means for maintaining the conditions of the ingredients being mixed in the mixing vessel and a third regulating means for maintaining the conditions of the starter culture in the at least one receiving reservoir.

The system preferably comprises a first propelling means for transferring mixed ingredients into each reservoir via the first manifold and a second propelling means for transferring the starter culture produced in the reservoir into the receiving container via the second manifold.

Ideally, the first regulating means comprises a first temperature regulating means for regulating processing temperature of the mixed ingredients and initiating culture being processed in the reservoir; the second regulating means comprise a second temperature regulating means for regulating temperature of the ingredients being mixed in the mixing vessel; and the third regulating means comprise a third temperature regulating means for regulating temperature of the starter culture in the receiving reservoir.

A temperature measuring means is ideally provided at each of the mixing vessel, reservoirs and the at least one receiving vessel.

Preferably, the first and the second propelling mean comprise first and second pumps respectively.

Conveniently, the first temperature regulating means comprises heating means and cooling means for regulating the temperature of the mixed ingredients and initiating culture being processed in each reservoir. The heating means may comprise a heating station having a water tank for heating water and a pipework which delivers the heat from the water in the tank to the reservoirs. The cooling means may comprise a cooling station which supplies a coolant to the tank via a cooling manifold.

In a preferred arrangement, the receiving container comprises a dosing vessel having measuring means from which dosing vessels required quantities of starter culture are transferred to further downstream processing steps. Such a dosing vessel may be located in an area remote from the reservoirs. However, a smaller tank may be located at each reservoir for local discharge of the contents of each reservoir.

In one application, the ingredients being mixed in the mixing vessel comprise at least one powdery ingredient and at least one liquid ingredient such as, for example, flour and an aqueous medium respectively for subsequent production of a starter culture, and most ideally, a starter culture for making dough for subsequent baking. The aqueous medium may comprise, for example, water or milk.

In a most preferred arrangement, the system comprises at least one storage container for storage of the powdery ingredient, the storage container being connected to the mixing vessel via a delivery means. The delivery means comprises a delivery manifold leading from the storage container to the mixing vessel, and the system further comprises a liquid manifold for supplying a liquid ingredient into the mixing vessel.

Ideally, the powdery ingredient is initially delivered from the storage container into an intermediate dosage container prior to its transfer into the mixing vessel. From the dosage container, the powdery ingredient is preferably delivered into the mixing vessel via a weight-difference measurement (loss-in-weight) mechanism.

Ideally, the first measuring means comprise a plurality of first weighing mechanisms each connected to one of the plurality of reservoirs; the second measuring means comprise a second weighing mechanism connected to the mixing vessel; the third measuring means comprise a third weighing mechanism connected to the at least one receiving vessel.

Advantageously, the system also includes a plurality of supply manifolds for delivering cleaning and rinsing fluids from a cleaning station to a plurality of locations in the system, and a plurality of return manifolds for collecting and returning said fluids from said plurality of locations back to said cleaning station. The system preferably includes spray means for spraying said fluids over components of the system at said plurality of locations.

Ideally, the electronic control means comprise a programmable logic controller (PLC) suitably programmed to read input signals from any of the first, second and third weighing means and from the temperature measuring means, to process the input signals and then send, if required, relevant output signals to any of the delivery means, the first and second propelling means and the first, second and third temperature regulating means to actuate said means in a manner which ensures:

provision of required quantities of ingredients in the mixing vessel;

maintenance of a pre-determined temperature of the ingredients being mixed in the mixing vessel;

delivery of required quantities of mixed ingredients at required times from the mixing vessel to the reservoir;

control of a pre-determined temperature of the mixed ingredients and initiating culture being processed in the reservoir; and provision of required processing time intervals, so as to obtain a starter culture having pre-determined properties.

The PLC is linked to a real time clock for use in conjunction with the PLC program.

Ideally, the PLC is programmable to actuate the cooling station in order to lower the temperature of the starter culture in a reservoir to retard or stop further fermentation in the reservoir.

Ideally, the PLC is programmable to control the second propelling means to discharge the starter culture produced in a reservoir, save for a portion of the starter culture which remains in the reservoir and is intended for a subsequent cycle of production of starter culture in this reservoir, the remaining portion being sufficient to serve as initiating culture for the subsequent cycle. A sensor means is provided connected between the reservoir and the PLC for enabling the PLC to determine the quantity of starter culture in the reservoir and preventing the quantity falling below a predetermined quantity on actuation of the second propelling means. This ensures that sufficient starter culture is retained in each reservoir to enable a desired amount of fresh culture to be prepared in that reservoir within a predetermined time.

The PLC is pre-programmed with information specifying the required amount of starter culture to be produced during a production run of the system.

In another aspect, the invention provides a method for producing dough starter culture in the above described system having a plurality of reservoirs comprising the steps of providing a plurality or reservoirs and:

a) pre-loading culture reservoirs with a desired amount of initiating culture maintained at an oppression temperature;

b) filling at least one first reservoir with a relevant amount of aqueous medium/flour mix;

c) allowing the contents of the first reservoir to ferment at a specified fermentation temperature for a pre-set fermentation time interval;

d) cooling the so obtained fermented starter culture in the first reservoir to an oppression temperature to stop the fermentation process;

e) discharging a desired first portion of the starter culture from the first reservoir whilst retaining a desired second portion therein, said retained second portion comprising an initiating culture for subsequent production in the first reservoir of a further batch of starter culture upon introduction of a next load of aqueous medium/flour mix;

f) upon expiry of a first pre-set delay interval from the start of fermentation in the first reservoir, filling a subsequent reservoir with the relevant amount of aqueous medium/flour mix;

g) allowing a second pre-set delay interval to elapse after the discharge before introducing the next load of aqueous medium/flour mix into the first reservoir; and h) repeating steps c) to f) in respect of the subsequent reservoir as if it were the first reservoir.

Preferably, the above steps are carried out continuously during a production run of the system.

Ideally, in the end of the production run a portion of the starter culture obtained in the last-used reservoir is retained for use as an initiating culture in a subsequent production run of the system. This portion of starter culture may be discharged locally into a smaller tank, collected and kept at an oppression temperature pending a next production run.

In a most preferred arrangement the number of reservoirs is eight, the fermentation time is preferably about twelve hours including filling and cooling time, the fermentation temperature is about 21° C. and the oppression temperature is about 16° C.

Ideally, the time allowed for discharging and using the produced starter culture from a reservoir, the first pre-set delay interval and the second preset delay interval are each about three hours.

Referring now to the drawings, the system for producing and handling starter culture according to the invention is generally indicated by reference numeral 1 (see FIG. 1). The system 1 is most suitable for and will be described in connection with producing and handling starter culture for subsequent use in baking of bread, pastries etc. Of course, the system of the invention is not limited for use only with such type of starter culture and, indeed, is suitable for or can be suitably adapted to producing and handling any type of flowing substances which require time- and condition-controlled management.

Figure 3:
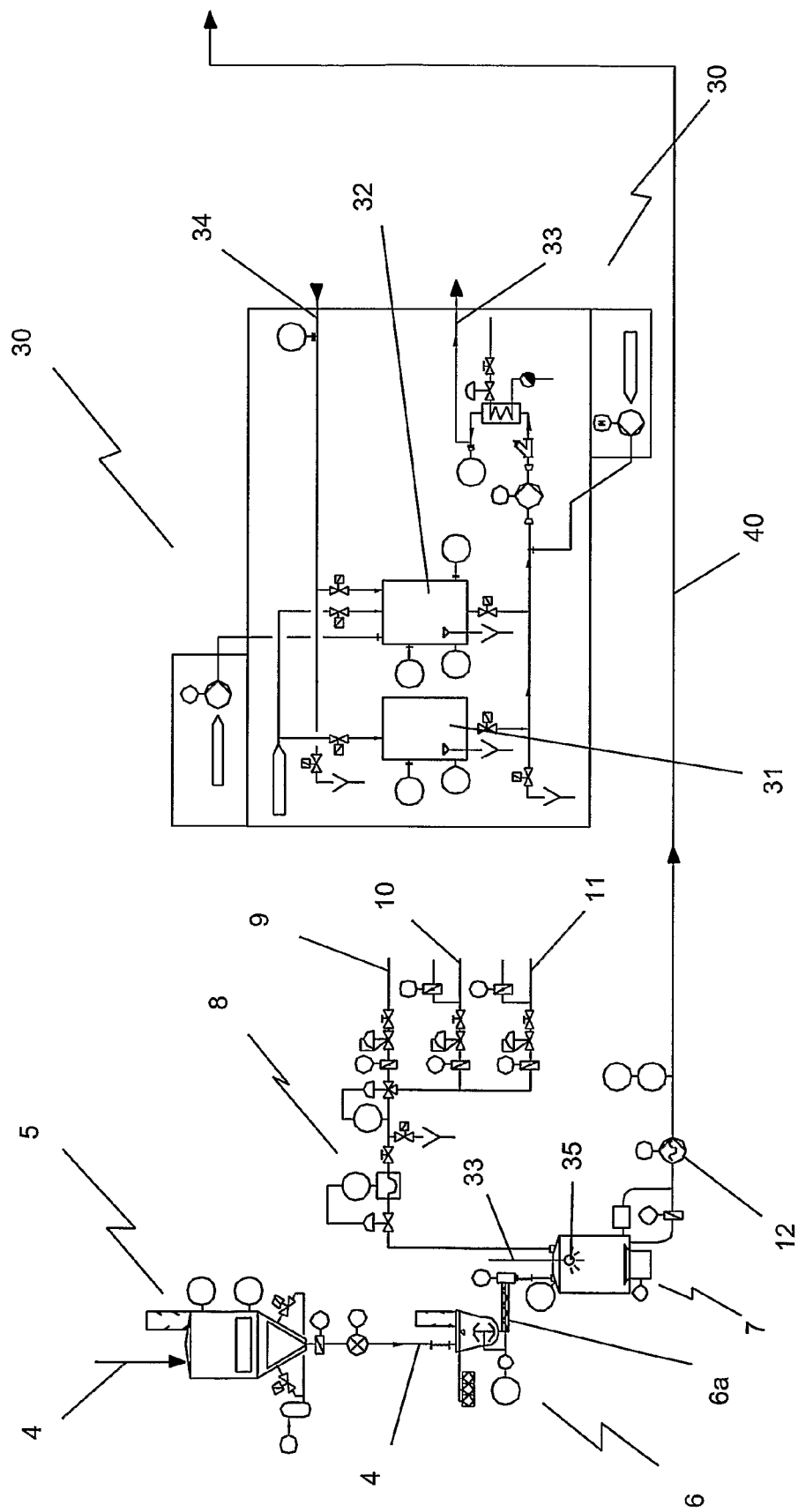
FIG. 3 is an enlarged portion of FIG. 1 showing a receiving hopper for flour, a mixing unit and a cleaning station of the system.
Figure 4:
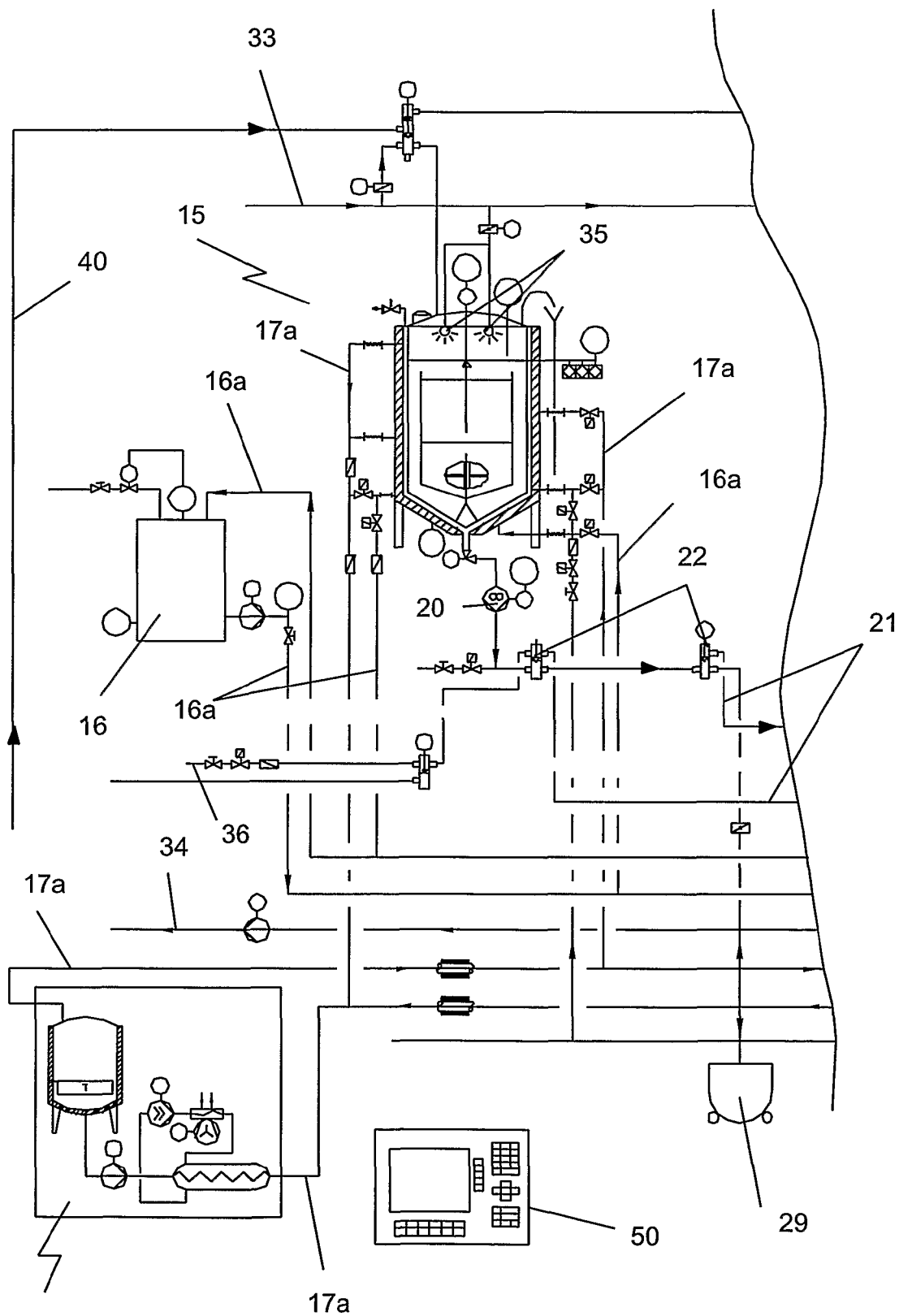
FIG. 4 is an enlarged portion of FIG. 1 showing a fermentation tank of the system.
Figure 5:
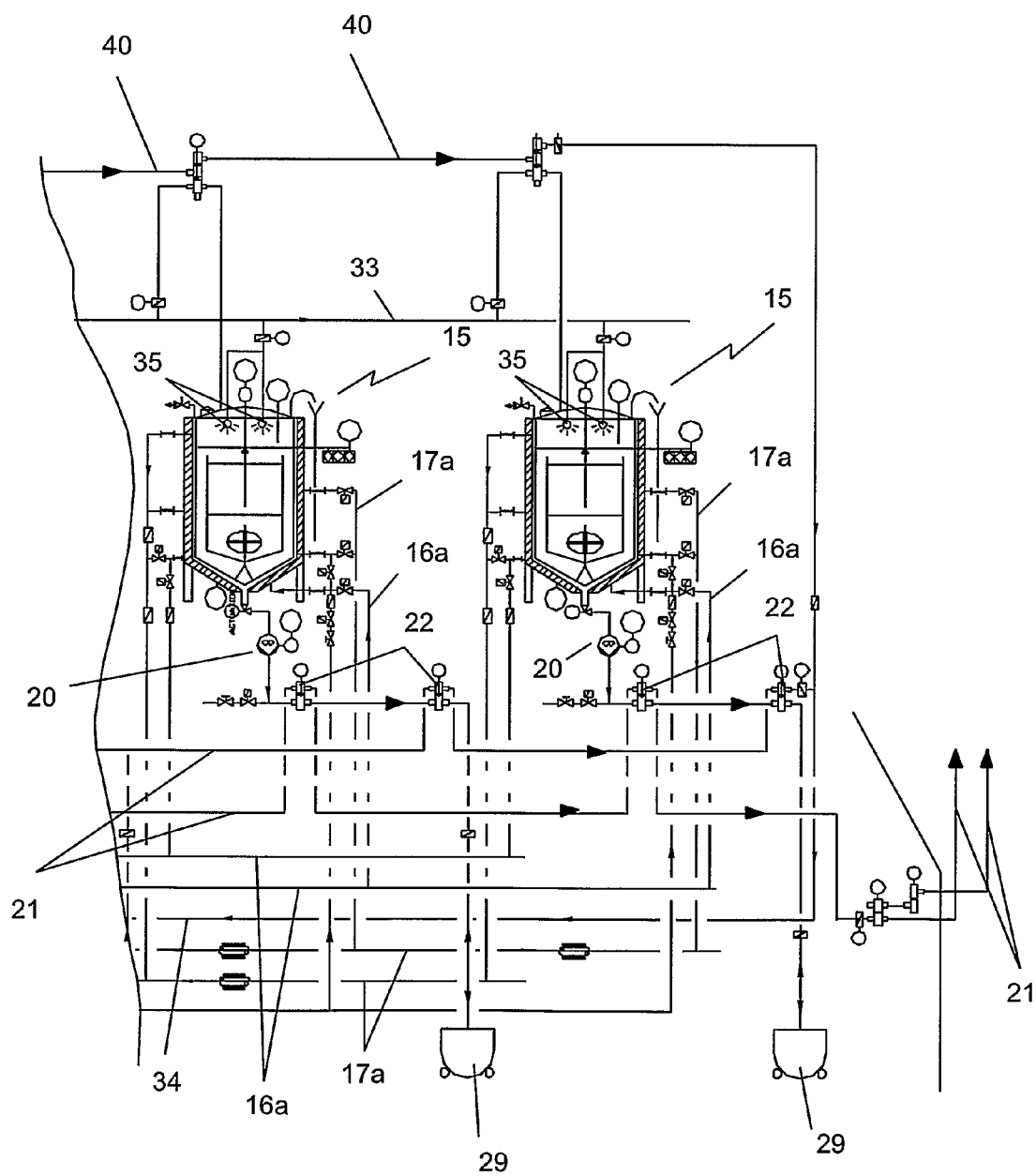
FIG. 5 is an enlarged portion of FIG. 1 showing another two fermentation tanks of the system and a portion of a manifold leading to further stages of handling of starter culture.
Figure 6:
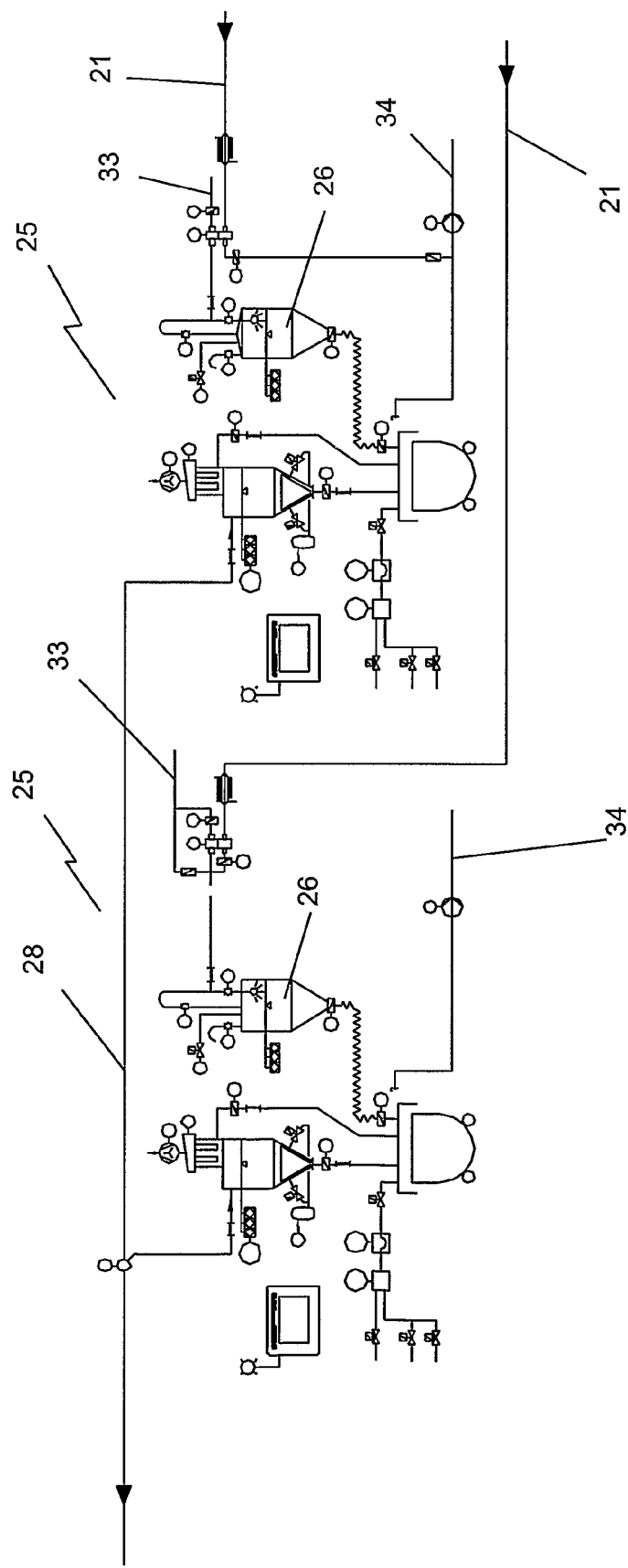
FIG. 6 is an enlarged portion of FIG. 1 showing two dosing stations of the system.

The system 1 comprises a storage container or a silo 2 in which a powdery ingredient, being flour in the present case, is stored. The flour is discharged from an outlet at the bottom of the silo 2 and received in a delivery manifold comprising a pneumatic conveying pipework 4. The flour passes through a sifter 3 into a receiving hopper 5 where a required quantity of flour for preparation of a batch of starter culture is accumulated. From the receiving hopper 5 the flour is discharged into a loss-in-weight screw feeder 6a (FIG. 3). A rotary valve 6 provides gradual feed of the flour from the hopper 5 to the screw feeder 6a. The screw feeder 6a delivers the flour into a mixing vessel or mixing unit 7 in which the flour is blended with an aqueous medium, for example plain water to form a uniform mix. The ratio between the quantities of flour and water dispensed depends on the recipe and can be, for example, 50% of water and 50% of flour. Water is maintained at a constant temperature, for example 21° C. (70° F.), by blending water from a mains water manifold 9, a chilled water manifold 10 and a warm water manifold 11. The quantity of water delivered into the mixing unit 7 is controlled by a flow-meter 8.

After the mix of flour and water is blended in the mixing unit 7, the mix is pumped by a pump 12 through a pipework 40 into a tank or reservoir 15. The tank 15 is selected from several such tanks employed in the system 1. The present system 1 has eight tanks 15 (although only three are shown), but of course any suitable number of tanks can be employed. Each tank 15 is installed on a load cell (not shown) which determines when the tank 15 is filled with the required quantity of the mix so that a signal can be given to the pump 12 to stop feeding the mix into the tank 15.

In the herein described system 1a certain amount of pre-prepared starter culture (initiating culture) is pre-loaded in the tanks 15 at the beginning of a production cycle of the tank before the flour/water mix is pumped into the tanks 15. This amount of initiating (starter) culture must not be less than a minimum amount for a given amount of flour/water mix. This minimum amount of initiating culture is known as a "mother level". The "mother level" of initiating culture depends on the recipe and can be, for example, 20% of an overall volume of an initial mixture of the "mother level" of initiating culture with the flour/water mix to be fermented in a tank 15. Thus, a tank 15 pre-loaded with 20% of "mother level" of initiating culture is filled with 80% of the flour/water mix to form the required overall quantity of the initial mixture to be fermented. Once the tank 15 is filled, the initial mixture of the "mother level" of initiating culture and the flour/water mix is left to ferment in the tank for a specified time according to the recipe, for example, twelve hours.

During the fermentation process, the temperature of the mixture in the tanks 15 is maintained at a constant predetermined level, which may be for example 21° C. (70° F.), at which the microorganisms of the "mother level" of starter culture become active and start to ferment the flour/water mix. This temperature of the contents of each tank 15 is brought to and maintained at the same level by supplying passing heated water to the tanks 15 from a water heater 16 via a heated water manifold 16a. During the fermentation process, the mixture is transformed into a starter culture which should be of the same characteristics as the initiating culture of the "mother level" in each tank 15.

In the herein described use of the system 1 for producing and handling starter culture, the starter culture resulting from the fermentation process needs to be cooled at the end of the fermentation process to an oppression temperature at which the microorganisms of the starter culture are inactive. Such temperature may be for example about 16° C. (60° F.) or less. A cooling station 17 is provided for lowering the temperature of the starter culture in the tanks 15 to the oppression temperature. The station 17 supplies coolant to the tanks 15 via a coolant supply manifold 17a.

The oppressed starter culture is discharged as required from each tank 15 via a discharge pump 20. The discharge pump 20 transfers the starter culture via a starter manifold 21 to dosing stations 25. Diverting valves 22 are provided in the manifold 21 for directing of the starter culture into a correct manifold of the system.

At each of the dosing stations 25 the starter culture is received in a receiving container, or a holding hopper 26. The holding hopper 26 is installed on a measuring means, such as a load cell (not shown) which determines when a batch of preset quantity of starter culture is delivered into the holding hopper 26 so that a signal can be given to the respective pump 20 to stop feeding the starter culture into the holding hopper 26. The holding hopper 26 stores the starter culture until the batch is required for further steps to be carried using the starter culture. For example, when a dough mixing system of a production line calls for ingredients for dough, the holding hopper 26 discharges the batch of starter culture via an outlet manifold 28 to a required location.

During a production run, the starter culture produced in the tanks 15 is not completely discharged from the tanks. A "mother level" of the starter culture is retained in each tank 15 for the next production cycle in that tank. At the end of a production period (perhaps a week), some starter culture is cooled to 16° C. (60° F.) and placed into a storage container 29 for use at the beginning of the next production week as a "mother level" for the tanks 15.

An example of a weekly scheme of operation of the system 1 for producing and handling starter culture will now be described below with reference to FIGS. 7 and 8. The scheme applies to an eight-tank system and can be altered to adapt to a system with different number of fermentation tanks 15. The fermentation time of twelve hours mentioned above for a single tank 15 is taken to include the time for filling the tank 15 with flour/water mixture and for cooling the contents of the tank 15 at the end of the fermentation process from 21° C. (70° F.) to 16° C. (60° F.). Of course, the system 1 is not limited to the scheme of operation described below and any other suitable way of organising the sequence of the steps of its operation ensuring continuous supply of freshly produced starter culture is possible.

At the start of a production week, the starter culture held over from the production run of the preceding week is split to provide "mother levels" in the eight tanks 15. If this quantity of starter culture is not sufficient to provide the necessary "mother levels" for all the tanks 15, then the starter culture needs to be built up prior to placement into the tanks 15 by adding a necessary amount of flour/water mix and fermenting for 12 hours in order to obtain an amount of the starter culture sufficient to be split amongst the tanks 15.

Referring to FIG. 7, at 100 Tank 1 is held pre-loaded with a "mother level" of starter culture at the beginning of a production cycle. The "mother level" quantity of starter culture is held at 16° C. (60° F.). At Time Zero, Tank 1 starts to be filled with flour/water mix at 21° C. (70° F.) and should be filled within 1 hour. At 101, Tank 1 is filled and the fermentation process begins. Ten hours later, at 102, the starter culture produced in Tank 1 during the fermentation process of the mixture of the "mother level" of starter culture with the flour/water mix is ready for use. At this stage the fermentation process is oppressed by cooling the starter culture to 16° C. (60° F.). The cooling process should be completed within one hour. This batch of starter culture is used within three hours. A "mother level" of the starter culture is retained in the tank 15 for the next production cycle of the tank 15. Upon expiry of the three hours for using the starter culture, another three hours elapses before introducing the next batch of flour/water mix into the tank 15 for the next production cycle. At 104, Tank 1 is ready for the next production cycle.

At 200, three hours after the beginning of the production cycle of Tank 1 i.e. from Time Zero, Tank 2, which is held pre-loaded with a "mother level" of starter culture, is filled with flour/water mix at 21° C. (70° F.) within one hour. Steps 201-204, which are the same as the steps 101-104 for Tank 1 are then followed.

FIG. 8 shows 24 hour schedules for Day 1 and Day 2 of the production cycles illustrated in FIG. 7 for eight tanks. A production cycle of each subsequent tank starts three hours after the beginning of the production cycle of a previous tank. The production cycles which have not completed at the end of Day 1 will continue to run during Day 2 until completed. The number of tanks in operation can be selected to match the requirement for starter culture batches needed to keep the downstream bakery adaptably supplied.

At the end of the production week the starter culture may be used entirely from all the tanks 15, except for one tank. The amount of the starter culture in the tank should be sufficient to be split amongst the eight tanks 15 and used as a "mother level" in the tanks during the production run of the next week. Alternatively, the remaining starter can be built up later by adding a necessary amount of flour/water mix as described above. The starter culture remaining from the production run may be pumped into a storage container 29 and stored at 16° C. (60° F.) so that the tank can be cleaned.

The system is cleaned using the known Cleaning-in-Place (CIP) technology. A commercially available CIP station 30 comprises a water tank 31 and a diluted detergent tank 32. The system 1 is adapted to be compatible with a known CIP station, such as the CIP station 30. Water and diluted detergent are mixed at the station and the mix is delivered to the components of the system 1 to be cleaned via a CIP supply manifold 33. After cleaning, the fluids are delivered back to the CIP station 30 via a CIP return manifold 34. Different components of the system 1 can be cleaned at different times and the components not engaged in an on-going production run can be cleaned during this production run. The manifolds 21 to the dosing stations 25 are cleaned only after a production run is completed.

A pre-programmed cleaning cycle is performed by the CIP station 30 for cleaning the tanks 15. The fluids are delivered into the tanks though spray balls 35 located at top regions of the tanks 15. The spray balls 35 of each tank 15 wash all parts of the interior of the tank. The fluids are drained from the tanks 15 via the discharge pumps 20. After passing through the discharge pumps 20 the fluids are directed by the diverting valves 22 into the return manifold 34 and are brought back to the CIP station 30. The CIP system 30 also provides hot or cold rinsing water to the tanks 15 in the above described manner. Air blow manifold 36 is provided to air purge the components of the system 1. Pipeworks 4 and 40 are also cleaned using a pre-programmed cleaning cycle by passing cleaning and rising fluids through the pipeworks and returning these fluids back to the CIP system 30.

The quantity of starter culture required weekly for a production run varies depending on the quantity of dough being produced for this production run. In the present system 1, a weekly production plan of dough governs the quantity of starter culture produced by the system 1.

Figure 9:
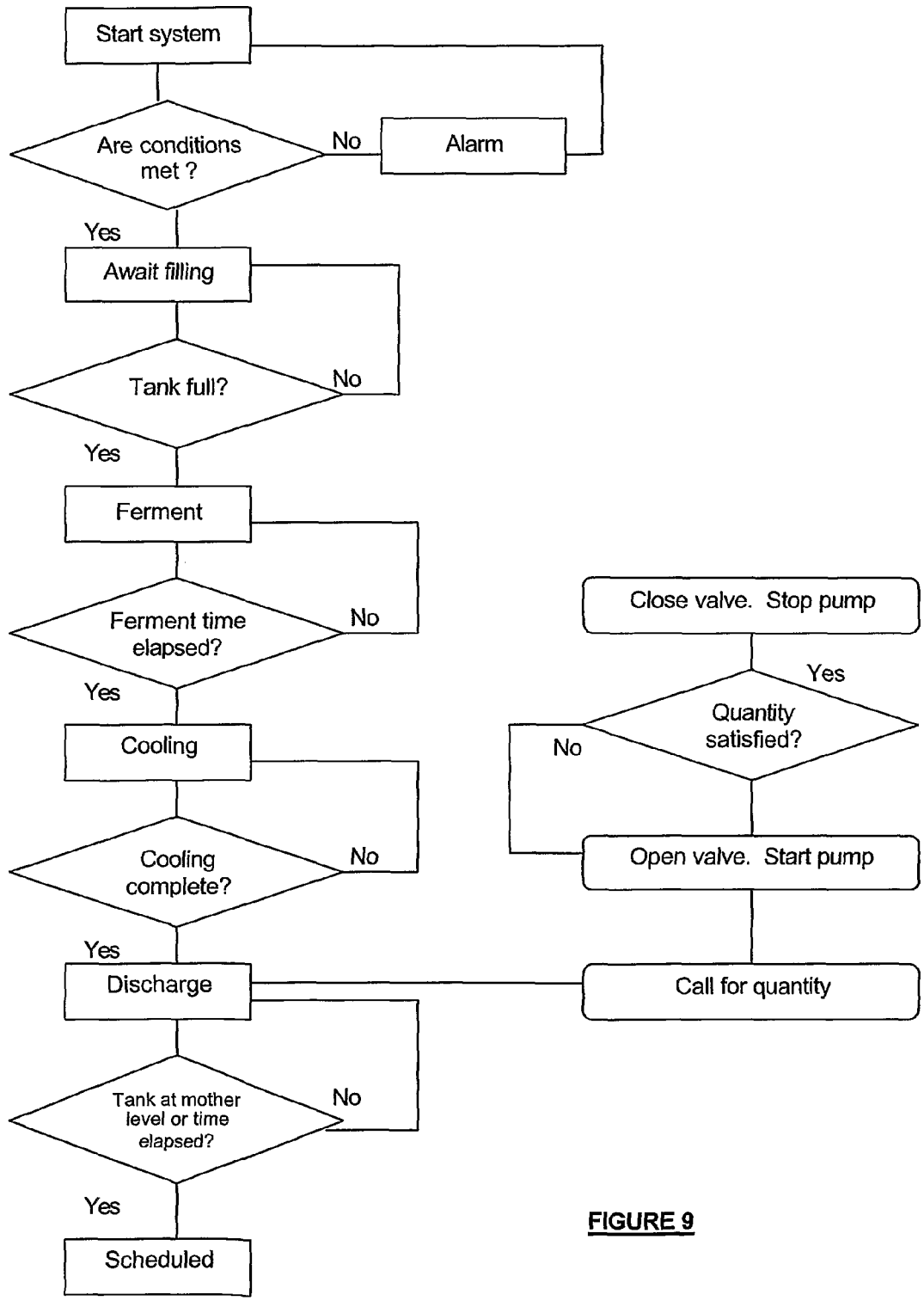
FIG. 9 shows a flow chart of a production cycle of a tank and its interactions with a system control unit.

The present system 1 is controlled using a programmable logic controller (PLC) which is suitably programmed to read input signals from various system components such as sensors, flow-meters, valves, pumps, load cells, etc., run control logic in respect of the input signals and then send output signals to the system to actuate a relevant system component and/or adjust relevant condition via a regulating device in order to ensure relevant production output in accordance with pre-inputted parameters of the production run. The PLC is linked to a real time clock for use in conjunction with the PLC program for sending output signals to the system at relevant times. One example of the interactions between the system and the PLC is shown in FIG. 9.

The sensors include, for example, a temperature sensor for the water supplied into the mixing unit 7, temperature sensors for measuring the temperature of the contents of the tanks 15 and holding hoppers 26. Sensors on valves and pumps determine the conditions of the valve or the pump, e.g. on/off, open/shut etc. Flow-meter 8 determines the quantity of water delivered into the mixing unit 7. Measuring means such as load cells (not shown) determine the quantity of material delivered into the tanks 15 and holding hoppers 26.

The regulating devices include, for example, flow-meters at water manifolds 9, and 11 which blend water from these three manifolds to achieve a desired water temperature of about 21° C. (70° F.) in the arrangement shown, heater 16 for maintaining the fermentation temperature in the tanks 15, cooling station 17, valves, pumps, etc.

The PLC allows the system to operate automatically during a production run, which could be a single run extending over several days. System conditions are operator-monitored by the use of one or more screens. One screen shows tank conditions such as "disabled", "await filling", "scheduled", "discharge", "cooling", "ferment".

If a tank is "disabled" then it is not included in the system for starter production. In the mode "await filling" the tank is being filled and is waiting for the fill cycle to complete within the allowed time of 1 hour for this example. In the "scheduled" mode, the tank has been scheduled for inclusion in the production system but has not yet received instructions for next use. In the "discharge" mode the tank is in use for discharge of the starter culture. In "cooling" mode the tank, which has gone through the fermentation time at the temperature of 21° C. (70° F.) is cooled to 16° C. (60° F.) to retard the fermentation. In "ferment" mode the tank is going through the fermentation process at 21° C. (70° F.). Also within this screen it is possible to view the quantity and temperature of the material in each tank and the fermentation time elapsed.

A set of screens is also provided which allows changes to be made to the times and temperatures of the tanks by manual intervention into the automatic run. This screen optionally has password protection and will normally only be accessible to an authorised person. For example, the fermentation temperature may be manually changed from 21° C. (70° F.) to 24° C. (75° F.).

A further screen or set of screens allow system parameters such as for example agitator speeds to be viewed and/or altered. Flour system screen allows such parameters as, for example temperature and quantity of flour in the silo 2 to be viewed.

Another screen is provided for viewing and adjusting the ratio of water/flour mix in the mixing unit 7, although normally the settings are made and never changed. Also it is possible to view the flow rates of flour and water.

A cleaning-in-place (CIP) control allows for the CIP system to be enabled or disabled.

Alarms screen shows any current and historic alarms that the system has experienced. It displays current alarms highlighted. Alarms may signal when motor overload occurs or when the temperature in tank 15 exceeds the permitted temperature. The alarms are acknowledged and/or attended to or by an operator depending on their severity.

The system also comprises a computer and specialised software to allow scheduling of starter production and graphic monitoring of the system. The computer does not in itself carry out any control function. An operator inputs a production schedule for finished products (e.g. bread) for a time period such as a week. The software already contains the recipes and calculates the amount of starter culture required and when it is required during the production run. The production schedule when downloaded to the PLC sets up particular quantities of starter culture that the tanks must produce to have sufficient quantity of starter culture ready at the appropriate times.

It will of course, be understood that the invention is not limited to the specific details described herein, which are given by way of example only and that various modifications and alterations are possible within the scope of the invention as defined in the appended claims.

The invention claimed is:

1. A system for producing and handling a flowing substance comprising:
   a mixing vessel for mixing ingredients for use in subsequent preparation of a flowing substance;
   a first manifold for transferring the mixed ingredients from the mixing vessel into one of a plurality of reservoirs where the mixed ingredients are combined with an initiating culture;
   first regulating means for maintaining predetermined conditions in each reservoir suitable to allow a fermentation process to occur which results in the production after a specified time of a starter culture as a flowing substance having predetermined properties from the initiating culture and the mixed ingredients;
   a second manifold for transferring the starter culture from each reservoir to at least one receiving container; and
   electronic control means for controlling the system so that the system provides delivery of mixed ingredients to each reservoir in a specified sequence so that a first pre-set interval of time elapses from the start of fermentation in a first or subsequent reservoir before the delivery of the mixed ingredients into a succeeding next reservoir, that interval being less than the fermentation time of the starter culture in the preceding reservoir,
   wherein the electronic control means is adapted to control the system so that the system effects discharge of a desired first portion of the starter culture from a reservoir whilst retaining a second portion therein, said retained second portion comprising an initiating culture for subsequent production in that reservoir of a further batch of starter culture upon introduction of a next load of the mixed ingredients; and to allow a second pre-set delay interval to elapse after the discharge before introducing the next load of the mixed ingredients into the reservoir;
   first propelling means for transferring mixed ingredients into each reservoir via the first manifold and second propelling means for transferring the starter culture produced in the reservoir into the receiving container via the second manifold,
   wherein the electronic control means is programmed to control the second propelling means to discharge the starter culture produced in a reservoir, save for the second portion of the starter culture which remains in the reservoir and is retained for a subsequent cycle of production of starter culture in this reservoir, the remaining second portion being sufficient to serve as initiating culture for the subsequent cycle; and
   a sensor means connected between the reservoir and the electronic control means for enabling the electronic control means to determine the quantity of starter culture in the reservoir and to prevent the quantity falling below a predetermined quantity on actuation of the second propelling means.

2. The system as claimed in claim 1, in which the electronic control means comprises a programmable logic controller (PLC).

3. The system as claimed in claim 2, in which the PLC is pre-programmed with information specifying the required amount of starter culture to be produced during a production run of the system.

4. The system as claimed in claim 1 comprising a plurality of reservoirs.

5. The system as claimed in claim 1 in which the ingredients being mixed in the mixing vessel comprise at least one powdery ingredient and at least one liquid ingredient.

6. The system as claimed in claim 5 in which, the powdery ingredient comprises flour and the liquid ingredient comprises an aqueous medium.

7. The system as claimed in claim 5, in which the system comprises at least one storage container for storage of the powdery ingredient, the storage container being connected to the mixing vessel via a delivery means, the delivery means comprising a delivery manifold leading from the storage container to the mixing vessel and the system further comprises a liquid manifold for supplying the liquid ingredient into the mixing vessel.

8. A method for producing a starter culture using the system of claim 1 comprising the steps of:
   a) pre-loading a plurality of reservoirs with a desired amount of initiating culture maintained at an oppression temperature;
   b) filling at least one first reservoir with a relevant amount of aqueous medium/flour mix;
   c) allowing the contents of the first reservoir to ferment at a specified fermentation temperature for a pre-set fermentation time interval to obtain a fermented starter culture;
   d) cooling the so obtained fermented starter culture in the first reservoir to an oppression temperature to stop the fermentation process;
   e) discharging a first portion of the starter culture from the first reservoir-whilst retaining a second portion therein, said retained second portion comprising an initiating culture for subsequent production in the first reservoir of a further batch of starter culture upon introduction of a next load of aqueous medium/flour mix;
   f) upon expiry of a first pre-set delay interval from the start of fermentation in the first reservoir, filling a subsequent reservoir with a relevant amount of aqueous medium/flour mix;
   g) allowing a second pre-set delay interval to elapse after the discharge before introducing the next load of aqueous medium/flour mix into the first reservoir; and
   h) repeating steps c) to f) in respect of the subsequent reservoir as if it were the first reservoir.

9. The method as claimed in claim 8 comprising the step of retaining at the end of the production run a portion of the starter culture obtained in the last-used reservoir for use as an initiating culture in a subsequent production run of the system.

10. The method as claimed in claim 9, in which the fermentation time is about twelve hours including filling and cooling time, the fermentation temperature is about 21° C. and the oppression temperature is about 16° C.

11. The method as claimed in claim 10, wherein the time allowed for discharging and using the produced starter culture from a reservoir, the first pre-set delay interval and the second preset delay interval are each about three hours.

* * * * *